United States Patent [19]

McAinsh et al.

[11] 4,138,475

[45] Feb. 6, 1979

[54] SUSTAINED RELEASE PHARMACEUTICAL COMPOSITION

[75] Inventors: James McAinsh; Raymond C. Rowe, both of Macclesfield, England

[73] Assignee: Imperial Chemical Industries Limited, London, England

[21] Appl. No.: 833,339

[22] Filed: Sep. 14, 1977

[30] Foreign Application Priority Data

Jun. 1, 1977 [GB] United Kingdom ............... 23114/77

[51] Int. Cl.$^2$ .................... A61K 9/52; A61K 9/54; A61K 9/58

[52] U.S. Cl. ...................................... 424/19; 424/20; 424/21

[58] Field of Search .................... 424/19–22, 424/35, 362

[56] References Cited

U.S. PATENT DOCUMENTS

| | | | |
|---|---|---|---|
| 2,853,420 | 9/1958 | Lowey | 424/35 X |
| 2,887,440 | 5/1959 | Greminger et al. | 424/362 X |
| 2,921,883 | 1/1960 | Reese et al. | 424/35 X |
| 2,928,770 | 3/1960 | Bardani | 424/35 X |
| 3,146,168 | 8/1964 | Battista | 424/362 X |
| 3,247,066 | 4/1966 | Milosovich | 424/20 X |
| 3,400,185 | 9/1968 | Kohnle et al. | 424/35 X |
| 3,492,397 | 1/1970 | Peters et al. | 424/20 |
| 3,835,221 | 9/1974 | Fulborth et al. | 424/20 |
| 3,917,813 | 11/1975 | Pederson | 424/20 |

OTHER PUBLICATIONS

Windholz et al., Merck Index 9th Ed. 1976, Merck & Co., Rahway, N. J. #7628, p. 1016, entry "Propranolol".

*Primary Examiner*—Shep K. Rose
*Attorney, Agent, or Firm*—Cushman, Darby & Cushman

[57] ABSTRACT

Sustained release pharmaceutical composition consisting of a hard gelatine capsule containing film coated spheroids, the spheroids comprising propranolol, or a pharmaceutically-acceptable salt thereof, in admixture with non-water-swellable microcrystalline cellulose, and the said spheroids having a film coat comprising ethylcellulose optionally together with hydroxypropyl methylcellulose and/or a plasticizer.

9 Claims, No Drawings

SUSTAINED RELEASE PHARMACEUTICAL COMPOSITION

This invention relates to a sustained release pharmaceutical composition and more particularly it relates to a sustained release pharmaceutical composition containing propranolol or a pharmaceutically-acceptable acid-addition salt thereof.

Propranolol hydrochloride is an important medicament which is widely used throughout the world. It is a $\beta$-adrenergic blocking agent which is mainly used for the treatment of angina pectoris, cardiac arrhythmias and hypertension. The chemical name for propranolol is dl-1-isopropylamino-3-(1-naphthoxy)-2-propanol. This compound and its acid-addition salts, and processes of manufacture thereof, are claimed in our United Kingdom patent No. 994,918. Furthermore, pharmaceutical compositions comprising at least one of these substances in admixture with a pharmaceutically-acceptable diluent or carrier are claimed in our United Kingdom patent No. 995,800. The present invention relates to a new sustained release pharmaceutical composition which is not disclosed in, nor rendered obvious by, said patent No. 995,800 nor elsewhere in the art.

According to the invention there is provided a sustained release pharmaceutical composition consisting of a hard gelatine capsule containing film coated spheroids, the said spheroids comprising, prior to coating, 40 to 65% by weight of propranolol or a pharmaceutically-acceptable acid-addition salt thereof in admixture with non-water-swellable microcrystalline cellulose, and the said spheroids having a film coat comprising ethylcellulose optionally together with hydroxypropyl methylcellulose.

The term "spheroid" is well known in the pharmaceutical art, and means a spherical granule having a diameter of approximately 0.5 to 2mm. As a particularly suitable salt of propranolol there may be mentioned, for example, the hydrochloride. A suitable microcrystalline cellulose is, for example, the material sold as Avicel-PH-101 (available from FMC Corporation, American Viscose Division, Avicel Sales, Marcus Hook, Pa, U.S.A.). According to one embodiment of the invention the uncoated spheroids may, for example, contain 50 to 60% by weight of propranolol hydrochloride and 50 to 40% by weight of microcrystalline cellulose, respectively.

A suitable form of ethylcellulose is that having a viscosity in the range of 5 to 100 cps at 20° C. (U.S. National Formulary XIII) (content of ethoxy groups 44 to 51% by weight), and more particularly a viscosity of 50 cps at 20° C. (content of ethoxy groups 48 to 49% by weight). A suitable form of hydroxypropyl methylcellulose is that having a viscosity in the range 3 to 100 cps at 20° C. (U.S. National Formulary XIII), and more particularly a viscosity of 6 cps at 20° C. The film coat may, for example, comprise 80 to 100% by weight of ethylcellulose and 20 to 0% by weight of hydroxypropyl methylcellulose, and more particularly 90% by weight of ethylcellulose and 10% by weight of hydroxypropyl methylcellulose. In addition, the film coat may optionally contain up to 20% by weight of a plasticizer, for example a vegetable oil, for example castor oil, or glycerol, or a glyceryl ester of a fatty acid, for example glyceryl triacetate or glyceryl monoricinoleate. The film coat may comprise 5 to 15% by weight of the coated spheroids, and preferably 9 to 10% by weight thereof.

The sustained release composition of this invention may, for example, contain 100 to 200mg., and more particularly 160mg., of the medicament, for example propranolol hydrochloride.

The sustained release compositions of this invention may be manufactured by well known pharmaceutical manufacturing methods. For example, the spheroids may be manufactured on a conventional spheroniser in which a horizontal, rough-surfaced plate rotates inside a stationary vertical cylinder, and then film coated in conventional manner in a perforated coating drum, and finally the film coated spheroids filled into hard gelatine capsules using a conventional encapsulation machine.

The invention is illustrated but not limited by the following Example.

EXAMPLE

Propranolol hydrochloride (60kg.) and microcrystalline cellulose (Avicel-PH-101; 40kg.) were blended together in a 450 litre planetary mixer. Water (50kg.) was added, and the mixer was run for 10 minutes until a homogeneous, plastic mass was obtained. The mass was extruded under pressure through a perforated cylinder to give cylindrical extrudates of nominally 1mm. diameter.

The damp extrudates (in batches of 15 to 20kg.) were placed in a spheroniser in which the rotating disc (diameter 68cm.) rotated at 300 to 400 r.p.m. The rotation was continued for 10 minutes, and the resulting spheroids were then dried at 60° C. in a fluidised bed drier. The dried spheroids were passed over a 1.4mm. screen, and those which passed through were subjected to a 0.7mm. screen. The over-and under-sized spheroids were discarded.

Acceptable spheroids (100kg.) were placed in a perforated coating drum fitted with a 0.5mm. screen and rotating at 17 r.p.m. A film formulation consisting of ethylcellulose (9kg.) and hydroxypropyl methylcellulose (1kg.) dissolved in a mixture of dichloromethane (100 liter) and methanol (100 liter) was sprayed onto the rotating spheroids at a rate of 750ml. per minute using a standard airless spray system. The resulting film coated spheroids were passed over a 1.4mm. screen to remove any aggregates, and then filled into hard gelatine capsules using a conventional encapsulation machine, such that each capsule contained 160mg. of propranolol hydrochloride. There was thus obtained a sustained release composition containing propranolol hydrochloride.

What we claim is:

1. A sustained release pharmaceutical composition consisting of a hard gelatine capsule containing film coated spheroids, the said spheroids comprising, prior to coating, 40 to 65% by weight of propranolol, or a pharmaceutically-acceptable acid-addition salt thereof, in admixture with non-water-swellable microcrystalline cellulose, and the said spheroids having a film coat comprising ethylcellulose or ethycellulose and hydroxypropyl methylcellulose.

2. The composition claimed in claim 1 in which the uncoated spheroids contain 50 to 60% by weight of propranolol hydrochloride and 50 to 40% by weight of non-water-swellable microcrystalline cellulose, respectively.

3. The composition claimed in claim 1 in which the film coat comprises 5 to 15% by weight of the coated spheroids.

4. The composition claimed in claim 1 in which the ethylcellulose has a viscosity of 50 cps at 20° C.

5. The composition claimed in claim 1 in which the hydroxypropyl methylcellulose has a viscosity of 6 cps at 20° C.

6. The composition claimed in claim 1 in which the film coat comprises 80 to 100% by weight of ethylcellulose and 20 to 0% by weight of hydroxypropyl methylcellulose.

7. The composition claimed in claim 1 in which the film coat contains up to 20% by weight of a plasticizer.

8. The composition claimed in claim 1 which contains 100 to 200 mg. of propranolol or a pharmaceutically-acceptable acid-addition salt thereof.

9. The composition claimed in claim 1 in which, prior to coating, the spheroids contain 60% by weight of propranolol hydrochloride in admixture with 40% by weight of non-water-swellable microcrystalline cellulose, and the spheroids have a film coat consisting of 90% by weight of ethylcellulose having a viscosity of 50 cps at 20° C. and 10% by weight of hydroxypropyl methylcellulose having a viscosity of 6 cps at 20° C., the film coat comprising 9 to 10% by weight of the coated spheroids, and the said composition containing 160 mg. of propranolol hydrochloride.

* * * * *